US006281394B1

(12) United States Patent
Oftring et al.

(10) Patent No.: US 6,281,394 B1
(45) Date of Patent: Aug. 28, 2001

(54) METHOD FOR PRODUCING VICINAL DIOLS OR POLYOLS

(75) Inventors: Alfred Oftring; Thomas Bogenstätter, both of Bad Dürkheim; Christian Ott, Speyer, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/508,506

(22) PCT Filed: May 16, 1998

(86) PCT No.: PCT/EP98/06130

§ 371 Date: Mar. 23, 2000

§ 102(e) Date: Mar. 23, 2000

(87) PCT Pub. No.: WO99/16733

PCT Pub. Date: Apr. 8, 1999

(30) Foreign Application Priority Data

Sep. 29, 1997 (DE) .............................................. 197 43 015

(51) Int. Cl.$^7$ ...................................................... C07C 27/00
(52) U.S. Cl. .............................................................. 568/858
(58) Field of Search ............................................... 568/858

(56) References Cited

FOREIGN PATENT DOCUMENTS

| 3229084 | * | 2/1984 | (DE) | ........................................ 31/20 |
| 2145076 | * | 3/1985 | (GB) | ........................................ 31/20 |

* cited by examiner

Primary Examiner—Johann Richter
Assistant Examiner—Elvis O. Price
(74) Attorney, Agent, or Firm—Oblon, Spivak, McClelland, Maier & Neustadt, P.C.

(57) ABSTRACT

A process for preparing vicinal diols or polyols from an organic reaction mixture containing formic esters of vicinal diols or polyols, in which water is added to the reaction mixture, without addition of bases, and the formic esters are hydrolyzed in a subsequent thermal treatment, the aqueous formic acid is removed, and vicinal diols or polyols remain behind.

16 Claims, No Drawings

METHOD FOR PRODUCING VICINAL DIOLS OR POLYOLS

This is the U.S. National Stage Application of PCT/EP98/06130 filed Sep. 25, 1998.

The invention relates to processes for preparing vicinal diols or polyols from olefins or formic esters of vicinal diols.

Vicinal diols can be prepared by reacting olefins with hydrogen peroxide and formic acid. This initially results in a mixture—depending on the ratios of the amounts of the starting materials—of vicinal diols and formic esters of the vicinal diols, it being possible for one or both of the hydroxyl groups to be esterified. In order to obtain the vicinal diols, the formic esters must be cleaved. A number of processes are known for this.

DE-A-23 29 084 describes a process for preparing vicinal diols and their formates wherein firstly olefins are reacted with formic acid and hydrogen peroxide, and the reaction product is reacted with catalytic amounts of alkali metal or alkaline earth metal alcoholates to cleave the esters.

DE-A-29 37 840 relates to a process for the hydroxylation of short-chain aliphatic mono- or diolefins. The mono- or diolefins are reacted with formic acid and hydrogen peroxide, and the reaction mixture is then neutralized with sodium hydroxide solution and extracted with ethyl acetate in order to obtain the required diols.

U.S. Pat. No. 4,479,021 relates to a continuous process for preparing 1,2-alkanediols. This entails reacting 1,2-olefins with formic acid and hydrogen peroxide, after which the resulting alkanediol monoformate is hydrolyzed in a multistage process. The hydrolysis is carried out by adding concentrated aqueous alkali solutions, after which the reaction product is extracted with an organic solvent.

GB-A-2 145 076 relates to a process for preparing 1,2-alkanediols. This entails reacting 1,2-olefins with hydrogen peroxide and formic acid, and hydrolyzing the resulting esters with 25% strength sodium hydroxide solution, after which the organic phase is distilled.

In the above processes, the hydrolysis or cleavage of the resulting formic esters is carried out with alkalis. The resulting diols are subsequently removed by extraction or distillation. On the one hand, the processes result in salts of formic acid which has to be removed and disposed of or worked up in an elaborate manner and, on the other hand, the removal of the vicinal diols from the reaction mixture is complicated.

It is an object of the present invention to provide processes for preparing vicinal diols or polyols in which no salts of formic acid are produced. It is additionally intended that the processes be simple to carry out and afford the required products in high yield.

We have found that this object is achieved by a process for preparing vicinal diols or polyols from an organic reaction mixture containing formic esters of vicinal diols or polyols, in which water is added to the reaction mixture, without addition of bases, and the formic esters are hydrolyzed in a subsequent thermal treatment, the aqueous formic acid is removed, and vicinal diols or polyols remain behind. The removal in this case is preferably effected by distillation.

The object is further achieved by a process for preparing vicinal diols or polyols from a reaction mixture containing formic esters of vicinal diols or polyols, in which methanol is added, in an amount which is at least stoichiometric relative to the formyl groups, to the reaction mixture, which is subsequently thermally treated with removal of methyl formate, methanol and water as azeotrope, and vicinal diols or polyols remaining behind.

The object is further achieved by a process for preparing vicinal diols or polyols by reacting olefins with hydrogen peroxide and formic acid to give a reaction mixture containing formic esters, where appropriate removing the aqueous phase and cleaving the formic esters, in which the cleavage is carried out by one of the above processes.

The object is additionally achieved by a process for preparing vicinal diols or polyols by reacting olefins which have at least 10 carbon atoms with hydrogen peroxide and formic acid to give a reaction mixture containing vicinal diols and formic esters, in which the reaction mixture is cooled, where appropriate after removal of the aqueous phase, whereupon the vicinal diols which have formed crystallize out, and the crystallized vicinal diols are removed mechanically.

It has been found according to the invention that in a process for preparing vicinal diols or polyols, it is possible for the cleavage of the resulting formic esters to be avoided or to be carried out by hydrolysis in the absence of bases. The processes according to the invention moreover lead in short reaction times to high conversions, high yields and pure products.

The processes according to the invention have the following advantages in particular:

quantitative conversion short reaction times products of high purity are obtained with high selectivity no isolation of the epoxide intermediate necessary no salt produced no (heavy) metal catalysis no organic solvents complete recycling respectively of the formic acid or of the formic acid/water azeotrope or of the methyl formate use of aqueous hydrogen peroxide as oxidizing agent no materials to be disposed of apart from the water produced.

The reaction of vicinal diols with hydrogen peroxide and formic acid will be described first.

Olefins which can be employed in the processes according to the invention are all olefins which can be reacted with hydrogen peroxide and formic acid. The olefins preferably have from 4 to 30+, particularly preferably 6 to 24, in particular 10 to 18, carbon atoms. They may be linear or branched olefins. It is preferred to employ linear olefins.

The olefins may contain one or more carbon-carbon double bonds. They preferably contain one carbon-carbon double bond, which may be terminal or internal. They preferably contain one terminal double bond. The olefin is moreover preferably linear.

The olefins which are employed may be unsubstituted but may also have substituents such as hydroxyl groups and/or functionalities from carboxylic or sulfonic acids, esters, aldehydes, ketones, ethers, halides, nitriles, amides, imides, amines (quaternary or protonated). The olefins are preferably unsubstituted.

Examples of suitable olefins are 1-hexene, 1-dodecene, 1-tetradecene, $C_{20-24}$-α-olefin, $C_{12-14}$-α-olefin which consists in particular of about ⅔ 1-dodecene and ⅓ 1-tetradecene.

It is also possible according to the invention to employ mixtures of olefins and crude products derived from the industrial synthesis of olefins.

The formic acid is usually employed as aqueous solution. This is preferably a concentrated aqueous solution containing from 50 to 100% by weight formic acid. Particularly employed are pure formic acid or an azeotrope of formic acid and water containing about 77% by weight formic acid.

The concentration of the hydrogen peroxide employed may vary within wide limits. The hydrogen peroxide is preferably employed in a concentration of at least 30%, particularly preferably of at least 50%. In place of formic acid it is also possible to use, for example, trifluoroacetic acid or a similar acid.

The molar ratio of olefin to formic acid to hydrogen peroxide in the reaction is preferably 1:0.3–10:1–4, particularly preferably 1:0.5–5:1–2. Particularly good results are obtained with molar ratios of 1:0.5–3:1–2. Examples of preferred molar ratios are 1:1:1, 1:2:1, 1:0.5:1–2, 1:3.5:2, 1:2:2, 1:2:1.5.

The content of formyl esters in the resulting reaction mixture increases with the content of formic acid in the reaction.

The reaction is preferably carried out at from 40 to 100° C., particularly preferably 80 to 100° C. under atmospheric pressure. The reaction can be carried out under elevated pressure. The reaction usually takes from 1 to 5 hours, preferably 2 to 4 hours. The reaction can moreover be carried out continuously or batchwise. The reaction is preferably carried out by mixing the olefin to be reacted with the selected amount of formic acid and, after heating to the reaction temperature, continuously adding the hydrogen peroxide. The hydrogen peroxide is preferably added at a rate of 0.1–10 ml/min, particularly preferably 0.1–4 ml/min, especially 1–2 ml/min, based on 50% strength $H_2O_2$ and 1 mol of olefin.

The reaction can, where appropriate, be carried out in the presence of catalytic amounts of a strong acid such as sulfuric acid or hydrofluoric acid.

The reaction is usually carried out in the absence of a solvent, apart from the water present in the reaction mixture. It is thus unnecessary to remove any organic solvent from the reaction mixture.

The reaction can be optimized by replacing part of the aqueous phase by concentrated formic acid during the reaction. A continuous process for concentrating the aqueous phase is possible.

The reaction usually results in a mixture which can be separated into an organic phase and an aqueous phase. For further workup, the aqueous phase, which contains excess formic acid, can be removed. The aqueous phase can be worked up, for example, by distillation to concentrate the formic acid, resulting in a formic acid/water azeotrope which can be returned to the reaction.

The reaction mixture can, where appropriate and preferably after removal of the aqueous phase, be worked up as follows:

Water can be added to the reaction mixture, without addition of bases, and subsequent thermal treatment be carried out. Since no bases such as alkali metal hydroxides are added there is no production of salts which would be difficult to remove from the reaction mixture and would have to be disposed of. Thus, after the addition of water, the reaction mixture is not basic but acidic. The amount of water added is preferably 0.5–20 times, particularly preferably 2–10 times, the weight of the organic phase. The hydrolysis step can be repeated after phase separation as often as required until the formation of diol or polyol is complete.

At this time, the reaction mixture preferably contains little or no free formic acid because it has preferably been removed previously with the aqueous phase.

The thermal treatment results in hydrolysis of the formic esters. The conditions for the thermal treatment are selected so that the temperature is in the range from 50 to 100° C., particularly preferably from 80 to 100° C., and the pressure is atmospheric. It is also possible to use a pressure in the range from 1 to 50 bar, particularly preferably 1 to 30 bar. It is correspondingly possible to reduce the reaction temperature at higher pressures.

The thermal treatment is moreover preferably carried out in such a way that the thermal stress on the reaction mixture is minimized. For this reason, the thermal treatment is preferably carried out in a thin-film evaporator, for example in a falling-film evaporator or wiped-film evaporator. A falling-film evaporator is particularly preferably employed. The residence time of the reaction mixture on the heated surface of the falling-film evaporator is preferably from 1 to 20 minutes, particularly preferably from 5 to 15 minutes.

It has been found that formic esters of the vicinal diols or polyols can be cleaved by the above thermal treatment without the need to add bases.

This workup is preferably carried out on a reaction mixture in which the conversion of the olefins is maximized in order to minimize the amount of olefins remaining in the product. The olefins may, where appropriate, be removed from the resulting vicinal diols or polyols by suitable processes.

If olefins having at least 10 C. atoms are employed for the reaction with hydrogen peroxide and formic acid, the mixture resulting from the reaction has a high content of vicinal diols and a relatively low content of formic esters. The reaction in this case is preferably carried out with a molar ratio of olefin to formic acid to hydrogen peroxide of 1:1.7:1.7.

The aqueous phase is preferably removed from the resulting reaction mixture and worked up as described above. The organic phase is then cooled, whereupon the vicinal diols which have formed crystallize out. The temperature for this is chosen to be below the melting point of the vicinal diols and, at the same time, the solubility of the vicinal diols. The crystallized vicinal diols are then removed from the organic phase mechanically, for example by centrifugation or filtration.

The organic phase (mother liquor) resulting after removal of the crystallized vicinal diols can, where appropriate after removing water and/or formic acid by distillation, be returned to the reaction. If the aqueous phase was removed before the crystallization, it is usually unnecessary to distil out water and/or formic acid. Since the mother liquor can be returned to the reaction, incomplete conversions are acceptable in this process variant. Unreacted olefins are returned to the reaction. The removed formic acid can likewise and preferably be returned to the reaction so that overall, as in the previous process, only excess water needs to be discharged.

The olefins employed in this process variant are preferably $C_{10-30+}$ olefins, in particular $C_{12-30+}$ olefins.

In the third process variant there is addition of methanol to a mixture obtained by reacting olefins with formic acid and hydrogen peroxide, preferably after removal of the aqueous phase. The amount of methanol in this case is at least stoichiometric relative to the formyl groups present in the reaction mixture (in free formic acid or in ester groups). The molar ratio of methanol to formyl groups is preferably from 50:1 to 1:1, particularly preferably from 30:1 to 5:1.

After the addition of methanol to the reaction mixture, it is thermally treated to transesterify the formic esters of the vicinal diols with methanol and convert free formic acid into the methyl ester. Then the methyl formate which has formed and any excess methanol and water which are present are distilled out as azeotrope. (The boiling point of methyl formate under atmospheric pressure is 32° C., and that of methanol is 65° C.). This is preferably done by heating the mixture under reflux. It is also possible to use elevated pressure. The thermal treatment and the heating for reaction with the methanol and for removal of the methyl formate formed can also take place in one step, ie. at the same time. The reaction can moreover be carried out as a type of reactive distillation in a suitable apparatus.

The resulting methyl formate can be returned directly to the synthesis of formic acid which goes through the stage of methyl formate. It is thus possible for the formic acid to be recovered in a simple manner in systems already existing and to be returned to the reaction.

The methanolysis of formic esters of vicinal diols from all the olefins mentioned above takes place rapidly and quantitatively. The process is thus universally applicable. In addition, it has the advantage that no formic acid is removed by distillation, especially when the aqueous phase is not removed before the methanolysis. Formic acid, or a formic acid/water mixture, is corrosive so that the apparatus used for removing it must consist of corrosion-resistant materials.

This process variant has the additional advantage that the methanolysis takes place distinctly faster than the hydrolysis. It is once again possible to add catalytic amounts of strong acids such as sulfuric acid or hydrofluoric acid in order to increase the reaction rate further.

In this variant of the preparation of vicinal diols, the reaction of the olefins is preferably complete so that no olefins remain in the mixture after the reaction.

In all process variants, the workup of the resulting formic esters of vicinal diols or of the vicinal diols takes place without the addition of bases and without the conditions being alkaline, preferably at a pH below 7.

The invention is explained in detail by means of Examples below.

EXAMPLE 1

Preparation of Formyl Esters (Olefin/Formic Acid Molar Ratio 1:2)

95.3 g (0.5 mol) of $C_{12/14}$-$\alpha$-olefin (consisting of about ⅔ 1-dodecene and about ⅓ 1-tetradecene) and 46.0 g (1.0 mol) of formic acid were introduced into a laboratory reactor. This mixture was heated to 100° C. and then 68.0 g (1.0 mol) of hydrogen peroxide as a 50% strength aqueous solution were added dropwise over a period of 5 to 6 hours (0.2 g/min). The mixture was then stirred at 100° C. for about a further 10 minutes until double bonds were no longer detectable (determined via the iodine value).

The organic phase was removed and used directly for the subsequent hydrolysis. Analysis of the organic phase showed the following:

Organic phase (145.4 g); acid value 1.632 mmol/g, water content: 14.0%, organic components: 28.2% formyl esters and 71.8% 1,2-diols.

Aqueous phase (23.2 g): acid value 5.230 mmol/g (excess formic acid).

Peroxide was no longer detectable.

EXAMPLE 2

Synthesis of Formyl Esters (Olefin/Formic Acid Molar Ratio 1:3.5)

95.3 g (0.5 mol) of $C_{12/14}$-$\alpha$-olefin and 80.5 g (1.75 mol) of formic acid were introduced into a laboratory reactor. This mixture was heated to 100° C. and then 68.0 g (1.0 mol) of hydrogen peroxide as 50% strength aqueous solution were added dropwise over a period of 105 minutes (0.65 g/min). The mixture was then stirred at 100° C. for about a further 40 minutes until double bonds were no longer detectable (determined via the iodine value).

The organic phase was removed and used directly for the subsequent hydrolysis. Peroxide was now detectable only in traces (0.013 mmol/g).

EXAMPLE 3

Synthesis of 1,2-diols 50 g of the formyl ester mixture from Example 1 or 2 were mixed with ten times the amount of water in a laboratory reactor. The mixture was refluxed with vigorous stirring for 17 hours. The hydrolysis was followed by chromatography.

EXAMPLE 4

The process of Example 1 was repeated but the olefin:formic acid:hydrogen peroxide molar ratio was 1:2:1.5. The rate of dropwise addition of the hydrogen peroxide was about 0.65 g/min. After 2.5 hours at 100° C. conversion was complete. The proportion of 1,2-diol was more than 80%.

EXAMPLE 5

The 1,2-diol present in the formyl ester mixture after the reaction is removed from the mixture by crystallization.

189.2 g (1.0 mol) of $C_{12/14}$-$\alpha$-olefin and 73.6 g (1.6 mol) of formic acid were introduced into a laboratory reactor. This mixture was heated to 100° C. and then 115.7 g (1.7 mol) of hydrogen peroxide (50% strength) were added dropwise over a period of 145 min, ie. at 1.05 g/min. The mixture was then stirred at 100° C. for about a further 60 min until double bond (iodine value) and peroxide were no longer detectable.

The complete reaction mixture was cooled to 10° C. 72 of this partly crystallized mixture were filtered off with suction through a grade 4 funnel maintained at 10° C.

The filter cake was then stirred with 100 ml of water (10° C.) for washing and was filtered off with suction.
Analysis of the Product Yield: 10.4 g (from the 72 g of reaction mixture employed) (94% 1,2-dodecanediol and 1,2-tetradecanediol, 6% formyl esters).

Acid value: 0.041 mmol/g, water: 27.0%.

EXAMPLE 6

189.2 g (1.0 mol) of $C_{12/14}$-$\alpha$-olefin (consisting of about ⅔ 1-dodecene and ⅓ 1-tetradecene) and 73.6 g (1.6 mol) of formic acid were introduced into a laboratory reactor. This mixture was heated to 100° C. and then 115.7 g (1.7 mol) of hydrogen peroxide (50% strength) were added dropwise over a period of 2 h, ie. at about 1 g/min. The mixture was then stirred at 100° C. for about a further 30 min until double bond (iodine value) and peroxide were no longer detectable.

Addition of 64.1 g (2.0 mol) of methanol and 0.1 g of concentrated sulfuric acid was followed by refluxing for 30 min and then removal of the methyl formate, methanol and water by distillation under atmospheric pressure.
Analysis Yield: quantitative 1,2-dodecanediol and 1,2-tetradecanediol. Acid value: 0.011 mmol/g, water content: 0.3%.

EXAMPLE 7

To hydrolyze the formyl esters, they were heated with three times the amount of water at 100° C. three times for 6 h each time.

189.2 g (1.0 mol) of $C_{12/14}$-α-olefin and 73.6 g (1.6 mol) of formic acid were introduced into a laboratory reactor. This mixture was heated to 100° C. and then 115.7 g (1.7 mol) of hydrogen peroxide (50% strength) were added dropwise over a period of 110 min, ie. at 1.05 g/min. The mixture was then stirred at 100 ° C. for about a further 45 min until double bond (iodine value) and peroxide were no longer detectable.

The lower aqueous phase was removed (80.4 g). Gas chromatogram of the organic phase: 74% diol and 26% formyl esters. The organic phase was heated with 380 g of water at 100° C. for 6 h. The lower aqueous phase was then removed. Gas chromatogram of the organic phase: 92.9% diol and 7.1% formyl esters, acid value: 0.144 mmol/g, water: 12.5%. The organic phase was heated for the second time with 380 g of water at 100° C. for 6 h. The lower aqueous phase was then removed. Gas chromatogram of the organic phase: 98% diol and 2% formyl esters, acid value: 0.102 mmol/g, water: 11.9%. The organic phase was heated for the third time with 380 g of water at 100° C. for 6 h. The lower aqueous phase was removed. The product was discharged at 80° C.

Analysis of the Product

Yield: 240 g (quantitative 1,2-dodecanediol and 1,2-tetradecanediol, no formyl ester). Acid value: 0.023 mmol/g, water: 11.7%.

We claim:

1. A process for preparing vicinal diols or polyols comprising:
    adding water to an organic reaction mixture comprising formic esters of vicinal diols or polyols, without addition of bases,
    hydrolyzing the formic esters in a subsequent thermal treatment,
    removing the aqueous formic acid, and
    recovering the vicinal diols or polyols.

2. A process for preparing vicinal diols or polyols comprising:
    adding methanol to a reaction mixture containing formic esters of vicinal diols or polyols, in an amount which is at least stoichiometric relative to the formyl groups, thermally treating said reaction mixture in the absence of base, removing methyl formate, methanol and water as an azeotrope, and recovering vicinal diols or polyols.

3. A process as claimed in claim 1, wherein the thermal treatment takes place in a thin-film evaporator.

4. A process as claimed in claim 2, wherein the thermal treatment takes place in a thin-film evaporator.

5. The process of claim 1, wherein said organic reaction mixture containing formic esters of vicinal diols or polyols is produced by a process of reacting olefins with hydrogen peroxide and formic acid to give a reaction mixture containing formic esters.

6. The process of claim 2, wherein said organic reaction mixture containing formic esters of vicinal diols or polyols is prepared by reacting olefins with hydrogen peroxide and formic acid to give a reaction mixture containing formic esters.

7. A process as claimed in claim 5, wherein the olefin is a $C_{6-30+}$ olefin.

8. A process as claimed in claim 6, wherein the olefin is a $C_{6-30+}$ olefin.

9. A process for preparing vicinal diols or polyols comprising reacting olefins which have at least 10 carbon atoms with hydrogen peroxide and formic acid to give a reaction mixture containing vicinal diols and formic esters in the absence of base,
    cooling said reaction mixture to form crystalized vicinal diols and a mother liquor
    and recovering the crystallized vicinal diols mechanically.

10. A process as claimed in claim 9, wherein the mother liquor resulting after removal of the crystallized vicinal diols is returned to said reaction mixture.

11. A process as claimed in claim 5, wherein the molar ratio of olefin to formic acid to hydrogen peroxide in the reaction is 1:0.3–10:1–4.

12. A process as claimed in claim 6, wherein the molar ratio of olefin to formic acid to hydrogen peroxide in the reaction is 1:0.3–10:1–4.

13. A process as claimed in claim 9, wherein the molar ratio of olefin to formic acid to hydrogen peroxide in the reaction is 1:0.3–10:1–4.

14. A process as claimed in claim 10, wherein the molar ratio is 1:0.5–5:1–2.

15. A process as claimed in claim 11, wherein the molar ratio is 1:0.5–5:1–2.

16. A process as claimed in claim 12, wherein the molar ratio is 1:0.5–5:1–2.

* * * * *

UNITED STATES PATENT AND TRADEMARK OFFICE
CERTIFICATE OF CORRECTION

PATENT NO. : 6,281,394 B1
DATED : August 28, 2001
INVENTOR(S) : Oftring et al.

Page 1 of 1

It is certified that error appears in the above-identified patent and that said Letters Patent is hereby corrected as shown below:

<u>Title page,</u>
Item [22], the PCT information should read:
-- [22] PCT Filed: Sep. 25, 1998

Signed and Sealed this

Twenty-sixth Day of February, 2002

Attest:

JAMES E. ROGAN
Attesting Officer   Director of the United States Patent and Trademark Office